United States Patent [19]
Miller et al.

[11] Patent Number: 5,626,132
[45] Date of Patent: May 6, 1997

[54] TRACHEAL TUBE WITH BUILT-IN VOCALIZATION CAPABILITY

[76] Inventors: Elizabeth L. Miller, 5231 Evonne Ave., Rohnert Park, Calif. 94928; Andras Westwood, 176 Wildhorse Valley Dr., Novato, Calif. 94947

[21] Appl. No.: 564,647

[22] Filed: Nov. 29, 1995

[51] Int. Cl.$^6$ .................. A61M 16/00; A62B 9/06
[52] U.S. Cl. .................. 128/207.14; 128/207.16; 128/207.17; 128/200.26; 623/9
[58] Field of Search ............ 128/207.14, 207.15, 128/207.16, 207.17, 200.26; 623/9; 604/96, 102, 180

[56] References Cited

U.S. PATENT DOCUMENTS

| | | | |
|---|---|---|---|
| 4,459,984 | 7/1984 | Liegner | 128/207.16 |
| 4,627,433 | 12/1986 | Lieberman | 128/207.16 |
| 4,633,864 | 1/1987 | Walsh | 623/9 |
| 4,649,913 | 3/1987 | Watson | 128/207.17 |
| 4,774,945 | 10/1988 | White et al. | 128/207.16 |
| 5,054,482 | 10/1991 | Bales | 128/207.17 |
| 5,054,484 | 10/1991 | Hebeler, Jr. | 128/207.16 |
| 5,123,922 | 6/1992 | Berg | 128/207.16 |
| 5,163,093 | 11/1992 | Frielingsdorf et al. | 381/151 |
| 5,285,777 | 2/1994 | Beckwith | 128/207.17 |

*Primary Examiner*—John G. Weiss
*Assistant Examiner*—Ki Yong O

[57] ABSTRACT

A tracheal tube with built-in vocalization capability including a neck piece having a bore disposed therethrough, ventilation holes disposed on the neck piece and around the bore, and a strap mechanism for securing the neck piece about a neck of a user to place the bore in general alignment with a stoma formed on the user's trachea; a rigid telescopically adjustable tubular throat piece with open ends bent in a general J-shaped configuration and having a lower straight portion insertable within the user's trachea through the stoma and an upper curved portion extended through the stoma and through the bore of the neck piece and secured to the neck piece; a flexible tubular first air line having an open distal free end, a sealed proximal end secured to an exterior surface of the throat piece, and a plurality of vent holes formed on the distal end for supplying air to vocal cords of the user; and a one-way air valve mechanism for controlling air flow through the first air line.

1 Claim, 5 Drawing Sheets

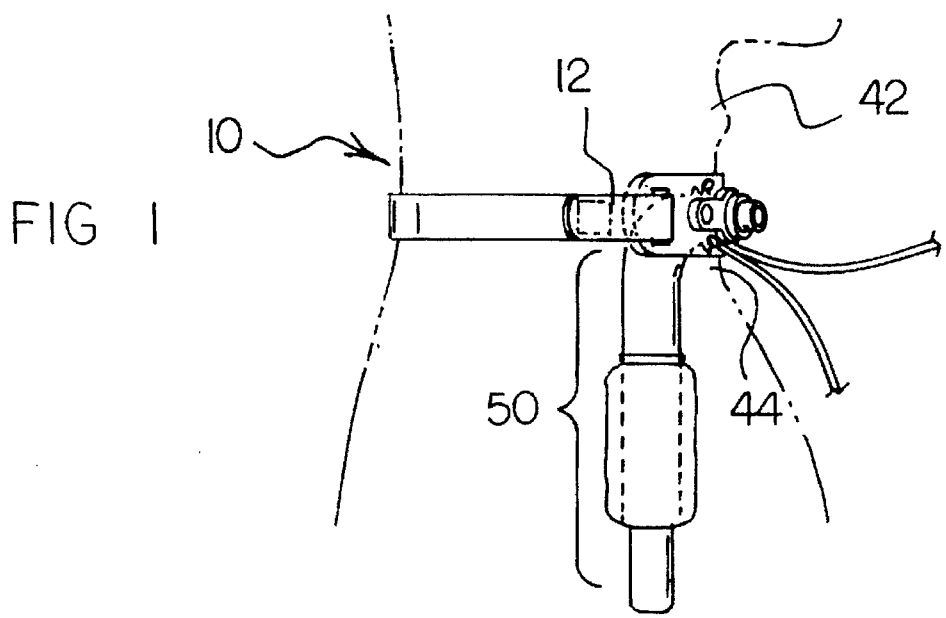
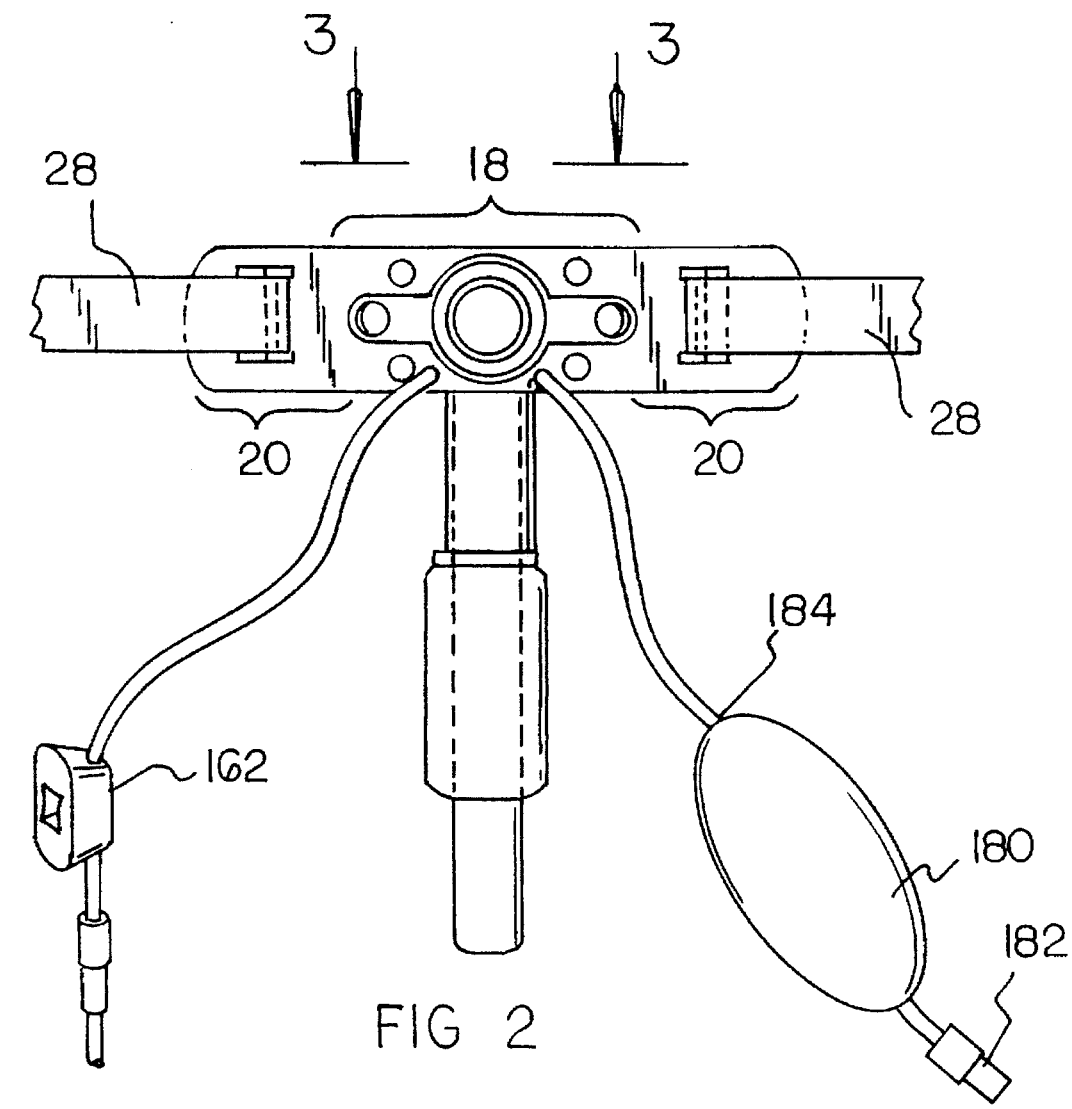

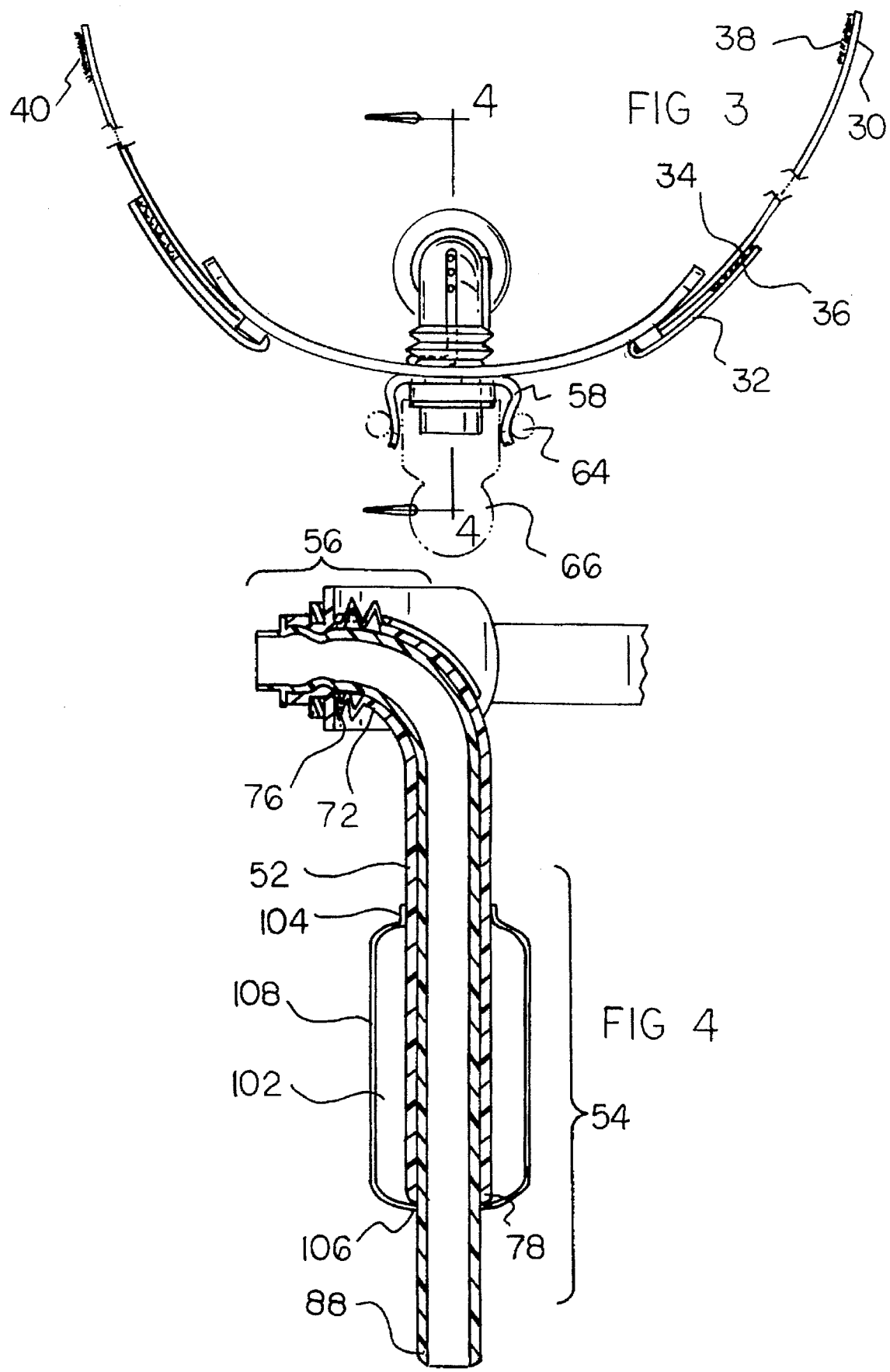

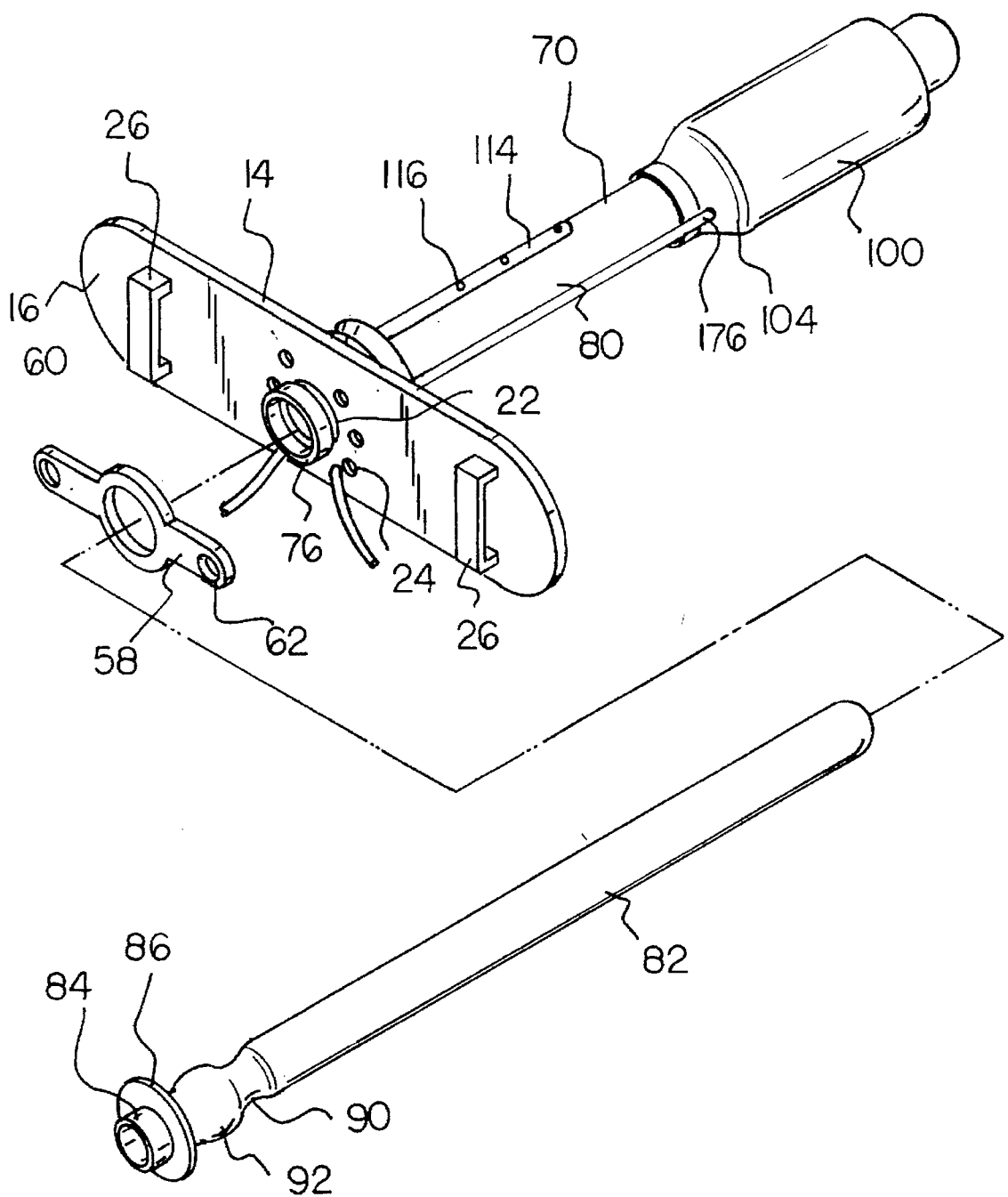

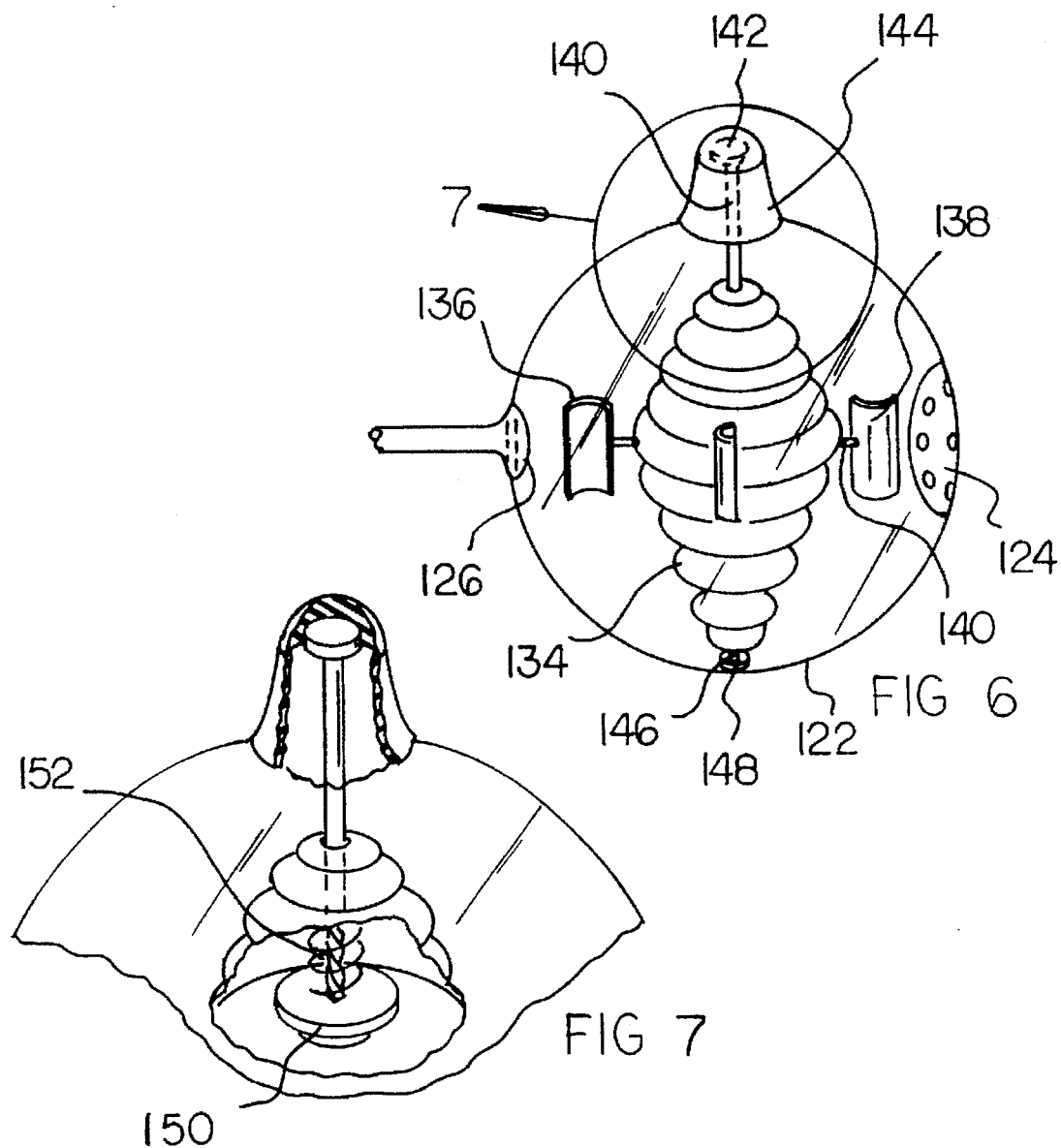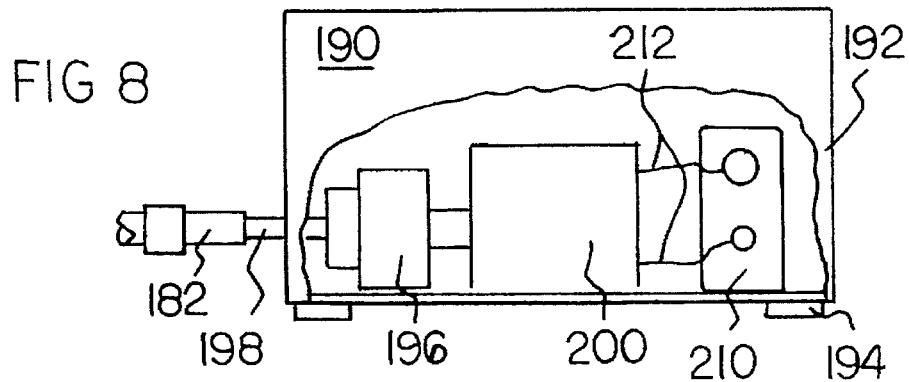

TRACHEAL TUBE WITH BUILT-IN VOCALIZATION CAPABILITY

BACKGROUND OF THE INVENTION

1. Field of the Invention

The present invention relates to a tracheal tube with built-in vocalization capability and more particularly pertains to allowing a user who has undergone a tracheotomy to breathe freely as well as speak with a tracheal tube with built-in vocalization capability.

2. Description of the Prior Art

The use of tracheal tubes is known in the prior art. More specifically, tracheal tubes heretofore devised and utilized for the purpose of allowing a user who has undergone a tracheotomy to breathe freely are known to consist basically of familiar, expected and obvious structural configurations, notwithstanding the myriad of designs encompassed by the crowded prior art which have been developed for the fulfillment of countless objectives and requirements.

By way of example, U.S. Pat. No. 3,090,380 to Dold discloses a resuscitation device. U.S. Pat. No. 3,118,596 to Saile discloses pumps. U.S. Pat. No. 3,363,833 to Laerdal discloses an elastic bag for an artificial respiration apparatus. U.S. Pat. No. 4,995,864 to Bartholomew et al. discloses a dual chamber pumping apparatus.

While these devices fulfill their respective, particular objective and requirements, the aforementioned patents do not describe a tracheal tube that allows a user to breathe freely as well as speak and is readily useable with conventional respiratory equipment. In this respect, the tracheal tube with built-in vocalization capability according to the present invention substantially departs from the conventional concepts and designs of the prior art, and in doing so provides an apparatus primarily developed for the purpose of allowing a user who has undergone a tracheotomy to breathe freely as well as speak.

Therefore, it can be appreciated that there exists a continuing need for new and improved tracheal tube with built-in vocalization capability which can be used for allowing a user who has undergone a tracheotomy to breathe freely as well as speak. In this regard, the present invention substantially fulfills this need.

SUMMARY OF THE INVENTION

In the view of the foregoing disadvantages inherent in the known types of tracheal tubes now present in the prior art, the present invention provides an improved tracheal tube with built-in vocalization capability. As such, the general purpose of the present invention, which will be described subsequently in greater detail, is to provide a new and improved tracheal tube with built-in vocalization capability and method which has all the advantages of the prior art and none of the disadvantages.

To attain this, the present invention essentially comprises, in combination, a generally oval planar neck piece having an inner surface, an outer surface, a resilient inner portion, a pair of integral and generally flexible opposed outer wing flaps extended outwards from each side of the inner portion, a central bore disposed therethrough, a plurality of ventilation holes disposed on the inner portion and around the bore, a strap anchor secured to the exterior surface of each wing flap, a pair of flexible straps with each strap having a distal free end and a proximal end secured to each strap anchor, a strip of pile-type fastener secured to one of the distal ends of one of the straps, and a complimentary strip of pile-type fastener secured to the other distal end of the other strap. The fasteners are securable in a closed loop configuration about a neck of a user to place the bore in alignment with a stoma formed on the user's trachea and to further place the inner surface of the neck piece in contact with the user's neck.

A flexible throat piece is provided and bendable in a general J-shaped configuration. The throat piece has a lower straight portion insertable within the user's trachea through the stoma and an upper curved portion extended through the stoma and through the bore of the neck piece and secured to the neck piece with a nut. The throat piece includes an outer cannula having a baffled open upper end with an outwardly projecting cylindrical lip disposed within the bore of the neck piece, an open lower end, and an intermediate portion therebetween. The throat piece includes an inner cannula slidably disposed within the outer cannula and having a flanged open upper end projected outwards from the upper end of the outer cannula, an open lower end projected outwards from the distal end of the outer cannula, and an intermediate necked portion therebetween. Lastly, the throat piece includes an air bladder having an upper extent secured around the intermediate portion of the upper cannula and a lower extent secured around the intermediate portion of the inner cannula. The bladder is inflatable with air for holding the throat piece in a fixed position within the user's trachea.

A flexible tubular first air line is provided and has an open distal free end, a sealed proximal end extended through the neck piece and secured to an exterior surface of the intermediate portion of the outer cannula, and a plurality of vent holes formed on the distal end for supplying air to vocal cords of the user. A one-way air valve is used for controlling air flow to the first air line. The air valve includes a rigid and generally spherical housing having an air inlet and an air outlet and with the air outlet secured to the free end of the first air line. The air valve also includes an axially aligned and spinable armature disposed within the housing. The armature has a hollow rigid central shell with a plurality of vanes extended outwards therefrom for directing air from the air inlet to the air outlet such as when a user inhales in preparation for speaking. The armature also has a rigid depressible upper pin extended outwards from the shell and through the housing, a rigid lower pin extended outwards from the shell and held in place against the housing, a clutch engaged with the upper pin, and a rigid worm drive engaged with the clutch and the shell. Depression of the upper pin allows the shell to be spun about an axis defined through the pins. A thumb clamp is also provided and coupled to the first air line. The thumb clamp has pair of jaws actuated through a lever for allowing crimping of the first air line to thereby control air flow to the user's vocal cords.

A flexible tubular second air line is included and has an open distal free end and an open proximal end extended through the neck piece and secured to the upper extent of the bladder for supplying air thereto. An air-fillable pilot balloon is included for providing an indication of a fill state of the bladder. The pilot balloon has a sealable inlet for receiving air and an outlet coupled to the distal end of the second air line. A pump is included and has an outlet securable to the inlet of the pilot balloon for filling it and the bladder with air.

A microphone is provided and coupled to the neck piece. The microphone is responsive to the user's voice. Lastly, an amplifier is included and coupled to the microphone. The amplifier is used for amplifying the user's voice.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved tracheal tube with built-in vocalization capability which has all the advantages of the prior art tracheal tubes and none of the disadvantages.

It is another object of the present invention to provide a new and improved tracheal tube with built-in vocalization capability which may be easily and efficiently manufactured and marketed.

It is a further object of the present invention to provide a new and improved tracheal tube with built-in vocalization capability which is of durable and reliable construction.

An even further object of the present invention is to provide a new and improved tracheal tube with built-in vocalization capability which is susceptible of a low cost of manufacture with regard to both materials and labor, and which accordingly is then susceptible of low prices of sale to the consuming public, thereby making such a tracheal tube with built-in vocalization capability economically available to the buying public.

Still yet another object of the present invention is to provide a new and improved tracheal tube with built-in vocalization capability which provides in the apparatuses and methods of the prior art some of the advantages thereof, while simultaneously overcoming some of the disadvantages normally associated therewith.

Even still another object of the present invention is to provide a new and improved tracheal tube with built-in vocalization capability for allowing a user who has undergone a tracheotomy to breathe freely as well as speak.

Lastly, it is an object of the present invention to provide a new and improved tracheal tube with built-in vocalization capability comprising a neck piece having a bore disposed therethrough, a plurality of ventilation holes disposed on the neck piece and around the bore, and strap means for securing the neck piece about a neck of a user to place the bore in general alignment with a stoma formed on the user's trachea; a flexible telescopically adjustable tubular throat piece with open ends bendable in a general J-shaped configuration and having a lower straight portion insertable within the user's trachea through the stoma and an upper curved portion extended through the stoma and through the bore of the neck piece; coupling means for securing the upper curved portion to the neck piece; a flexible tubular first air line having an open distal free end, a sealed proximal end secured to an exterior surface of the throat piece, and a plurality of vent holes formed on the distal end for supplying air to vocal cords of the user; and one-way air valve means coupled to the first air line for controlling air flow therethrough.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side-elevational view of the preferred embodiment secured to a user's trachea and neck.

FIG. 2 is another side-elevational view of the preferred embodiment of the present invention.

FIG. 3 is a view of the present invention taken along the line 3—3 of FIG. 2.

FIG. 4 is a cross-sectional view of the present invention taken along the line 4—4 of FIG. 3.

FIG. 5 is an enlarged perspective view of a portion of the present invention with its inner cannula removed.

FIG. 6 is a view of a one-way check valve of the present invention.

FIG. 7 is an enlarged fragmentary view of the armature of the one-way check valve.

FIG. 8 is a view of the electric air pump of the present invention.

The same reference numerals refer to the same parts through the various Figures.

DESCRIPTION OF THE PREFERRED EMBODIMENT

Figure 9:
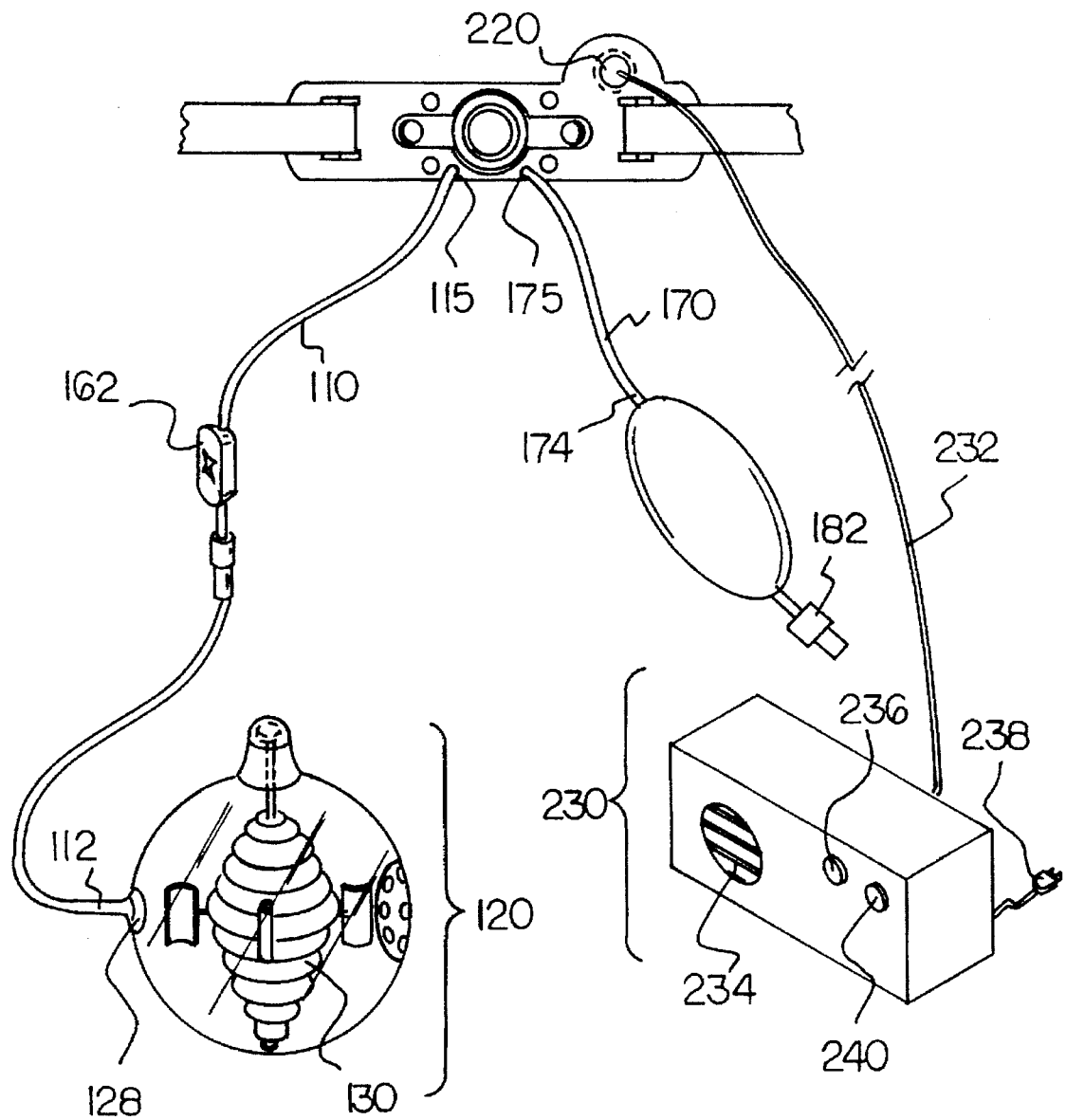
FIG. 9 is a view of an alternate embodiment of the present invention with a microphone and amplifier arrangement secured thereto for amplifying a user's voice.

With reference now to the drawings, and in particular, to FIG. 1 thereof, the preferred embodiment of the new and improved tracheal tube with built-in vocalization capability embodying the principles and concepts of the present invention and generally designated by the reference number 10 will be described.

The preferred embodiment of the present invention comprises a plurality of components. In their broadest context, such components include a neck piece, throat piece, air lines, air valve, thumb clamp, pilot balloon, air pump, microphone and amplifier. Such components are individually configured and correlated with respect to each other to provide a structure that allows a user who has undergone a tracheotomy to breathe freely as well as speak.

Specifically, the present invention includes a general oval and planar neck piece 12 formed of plastic or other suitable elastomeric material. The neck piece has an inner surface 14, an outer surface 16, and a peripheral edge interconnecting the surfaces. The neck piece also includes a substantially rectangular resilient inner portion 18 and a pair of integral and generally flexible opposed outer wing flaps 20 extended outwards from each side of the inner portion. A central circular bore 22 is disposed through the neck piece, and a plurality of ventilation holes 24 are disposed on the inner portion 18 and around the circular bore 22. Each ventilation hole 24 has a diametric extent that is less than that of bore 22. A generally U-shaped rigid strap anchor 26 is secured to the exterior surface of each wing flap 20.

In addition, a pair of flexible nylon or fabric straps 28 are provided. Each strap has a distal free end 30 and a proximal end 32. The proximal end of each strap is removably secured to a separate strap anchor in a loop configuration with a strip of pile-type fastener 34 and a complimentary strip of pile-type fastener 36. Strips 34 and 36 are sewn to opposing portions of each individual strap. Furthermore, a strip of pile-type fastener 38 is sewn to one of the distal ends of one of the straps, and a complimentary strip of pile-type fastener 40 is sewn to the distal end of the other strap. The fasteners 38, 40 are removably securable in a closed loop configuration about a neck 42 of a user to place the bore 22 in alignment with a stoma (not illustrated) formed on the user's trachea 44 and to further place the inner surface 40 of the neck piece in facing form-fit contact with the user's neck.

A non-flexible or rigid throat piece 50 is provided. The throat piece 50 is bent in a general J-shaped configuration 52. The throat piece has a lower straight portion 54 that is insertable within the user's trachea through the stoma and an upper curved portion 56 that is extended outwards from the stoma and through the bore 22 of the neck piece. The curved portion 56 is then removably secured to the neck piece 12 with a plastic nut. The nut includes an annular central portion with two diametrically opposed and eyelets 60 formed thereon. The eyelets permit ease of insertion of external trachea tie flaps 64 for holding an external oxygen source 66 in a stationary position for use by the user. The throat piece includes an outer cannula 70. The outer cannula has an open upper end 72 with a flexible telescoping baffled portion 74 formed thereon and is terminated with an outwardly projecting smooth cylindrical lip 76. Lip 76 is slidably and frictionally disposed through the bore 22 of the neck piece. The outer cannula 70 also has an open lower end 78 and an intermediate portion 80 extended between the upper end 72 and lower end 78.

Slidably and telescopically disposed within the outer cannula 70 is an inner cannula 82. The inner cannula has an open upper end 84 projected outwards from the upper end of the outer cannula with a flanged portion 86 formed at a location intermediate thereto. The inner cannula 82 also has an open lower end 88 that is projected downwards and outwards from the distal end 78 of the outer cannula. An intermediate necked portion 90 is formed between the ends 86, 88 and thus creates a bulb-like projection 92. In addition, the throat piece 50 includes an air bladder 100. The air bladder has a hollow interior 102 that is fillable with air. The bladder has an upper extent 104 secured around the intermediate portion of the upper cannula and a lower extent 106 secured around the intermediate portion of the inner cannula at a location adjacent to the lower end 78 of the outer cannula. Such securement can be formed with an adhesive weld or the like. The bladder is inflatable with air for holding the throat piece 50 in a fixed position within the user's trachea 44. The air bladder also includes a smooth tubular intermediate extent 108 that is extended between the upper and lower extents 104, 106.

A flexible tubular rubber first air line 110 is included and has an open distal free end 112 and a sealed proximal end 114. The proximal end is extended through the neck piece 12 through a bore 115 and secured to an exterior surface of the intermediate portion 80 of the outer cannula 70 at the curved portion 18. A plurality of linear and spaced vent holes 116 are formed on the distal end 112 for supplying air to the vocal cords (not illustrated) of the user.

To control air flow through the first air line 110, a one-way air valve 120 is provided. The air valve 120 includes a rigid, hollow, and generally spherical transparent plastic housing 122. Housing 122 has an air inlet 124 and an air outlet 126 formed thereon in diametric opposition. The air outlet 122 is secured to the free end 112 of the first air line with a seal 128. Disposed within the housing is an axially aligned and spinable armature 130. The armature includes a hollow, rigid, and centrally positioned plastic elongated shell 132 formed of a plurality of concentrically aligned and stacked annular-shaped sections 134. The sections have diametric extents that gradually increase from one end of the shell to a central location and then gradually decrease to the other end. Four vanes 136 are extended outwards from the shell at right angles for directing air from the air inlet 124 to the air outlet 126 such as when a user inhales in preparation for speaking. Each vane is formed of a bended rectangular blade section 138 and integral linear support post 140. A rigid depressible pin 140 is extended axially outwards from the shell and through the housing and is then terminated at a head 142. Head 142 is encased in a transparent elastomeric cap 144. A rigid lower pin 146 is also extended axially outwards from the other end of the shell and terminated at a head 148. The head 148 is held in place against an interior surface of the housing 122. In addition, a clutch 150 is engaged with the upper pin through a rigid metal worm drive 152. The worm drive is also engaged with the upper pin 140. When the head 142 of the upper pin is depressed, the shell can be spun about an axis defined through the pins, thereby allowing the vanes to direct air to the first air line 110 for delivering air to a user's vocal cords, the faster and harder we depress, the more flow we create. When the head 142 is not depressed, rotation of the shell is prohibited.

Coupled to the first line 110 is a plastic thumb port 162 thereby controlling of air flow to the user's vocal cords.

Also provided is a flexible tubular plastic second air line 170. The second air line has an open distal free end 174 and an open proximal end extended through a bore 175 on the neck piece 12 and then secured to the upper extent 104 of the bladder. The second air line supplies air to the bladder for its filling. In association with the second air line is an air-fillable plastic pilot balloon 180. The pilot balloon is used for providing an indication of a fill state of the bladder 100 to a user or other individual. The pilot balloon has a sealable syringe-type inlet 182 that is used for receiving air and an outlet 184 removably coupled to the distal end 174 of the second air line 170.

An electric air pump 190 is used for providing air for filling the pilot balloon 180 as well as the bladder 100. The air pump has a hollow and box-shaped rigid metal housing 192 with a plurality of feet 194 extended downwards therefrom and positionable upon a recipient surface. The air pump includes a pneumatic diaphragm 196 with an outlet 198 removably securable to the inlet 182 of the pilot balloon. A motor 200 is engaged with the pneumatic diaphragm 196 and is powered with a battery 210. The battery is connected to the motor for providing electrical energy thereto for operation through conducting lines 212. The battery is removable from the housing through an access door (not illustrated).

In addition, an electronic microphone 220 is coupled to the neck piece 12. The microphone is responsive to the user's voice when the user is speaking with air supplied through the first line as previously described. An amplifier 230 is also coupled to the microphone 220 with a conducting cable 232. The amplifier is used for electronically amplifying the user's voice, since a user's voice through use of the present invention is typically generated only at a whisper level. The amplifier includes amplifier circuitry (not illustrated), a speaker 234 for projecting audible sound to a remote location, and a dial 236 for controlling sound volume. A power cable 238 for providing electrical energy is included and is removably securable to an external power source through a plug. A depressible power button 240 is coupled between the power cable and the amplifier circuitry and controls or prevents electrical energy from being delivered upon discretion of the user.

The present invention is a design that provides several features that improve patient comfort as well as ease of care. The present invention allows patient vocalization even when with the pilot balloon 180 is inflated, in contrast to older designs. The nut 58 of the neck piece includes two diametrically opposed and flexible eyelets extended therefrom to allow ease of insertion of external trachea tie flaps for holding an oxygen source. The neck piece features ventilation holes 24 positioned around the throat piece that allow one to secure an external trachea swivel used with conventional mechanical ventilators. This feature precludes the use of conventional rubber bands which can cause uneven pull or torque of conventional throat pieces and thereby cause misalignment within a user's trachea. The air lines are positioned off-axis from the throat piece so that conventional taping of the lines to the throat piece is thus avoided. Behind the flange 86 is the beveled telescopic or movable portion of the throat piece. This feature allows forward movement of the throat piece by approximately ½ inch to allow ease in removal and replacement of trachea dressings. The canulas are slidable with respect to each other by a distance of about ½ inch. The inner canula has a lip at the distal end thereof to prevent it from being removed from the outer cannula. The flange on the upper end of the inner cannula is 1/32 inch thick and extends radially outwards by a distance that is ¼ inch greater than an outer diameter of the upper end of the outer cannula. The flanged portion 86 prevents the inner cannula from being accidentally pushed into the stoma or tracheal opening.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A tracheal tube with built-in vocalization capability for allowing a user who has undergone a tracheotomy to breathe freely as well as speak comprising, in combination:

a generally oval planar neck piece having an inner surface, an outer surface, a resilient inner portion, a pair of integral and generally flexible opposed outer wing flaps extended outwards from each side of the inner portion, a central bore disposed through the neck piece, a plurality of ventilation holes disposed on the inner portion and around the bore with the ventilation holes having a diametric extent that is less than that of the bore, a strap anchor with U-shaped configuration secured to an exterior surface of each wing flap, a pair of flexible straps with each strap having a distal free end and a proximal end secured to each strap anchor, a strip of pile-type fastener secured to one of the distal ends of one of the straps, and a complimentary strip of pile-type fastener secured to the other distal end of the other strap and with the fasteners securable in a closed loop configuration about a neck of a user to place the bore in alignment with a stoma formed on a user's trachea and to further place the inner surface of the neck piece in contact with a user's neck;

a flexible throat piece bent in a general J-shaped configuration with a lower straight portion insertable within the user's trachea through the stoma and an upper curved portion extended through the stoma and through the bore of the neck piece and secured to the neck piece with a nut having an annular central portion with two diametrically opposed eyelets formed thereon which permit ease of insertion of external trachea flaps for holding an external oxygen source in a stationary position for use, the throat piece including:

an outer cannula having a baffled open upper end with an outwardly projecting cylindrical lip disposed within the bore of the neck piece, an open lower end, and an intermediate portion therebetween, an inner cannula slidably disposed within the outer cannula and having a flanged open upper end which extends radially ¼ an inch with a thickness of 1/32 inch, the flanged open upper end projected outwards from the upper end of the outer cannula, an open lower end projected outwards from a distal end of the outer cannula, an intermediate necked portion therebetween thereby creating a bulb-like projection, wherein behind the flanged open upper end, is a movable portion which allows forward movement of the throat piece by about ½ inch with respect to the outer canula to allow ease in removal and replacement of conventional trachea dressings; and an air bladder having an upper extent secured around the intermediate portion of the upper cannula, a lower extent secured around the intermediate portion of the inner cannula, and a smooth intermediate portion, wherein the bladder inflatable with air for holding the throat piece in a fixed position within the user's trachea and said securement is accomplished with an adhesive;

a flexible tubular first air line having an open distal free end, a sealed proximal end extended through the neck piece and secured to an exterior surface of the intermediate portion of the outer cannula, and a plurality of linearly aligned and a spaced vent holes for allowing the supply of air to vocal cords of the user, wherein the flexible first air line is off set with respect to the central bore of the neck piece;

a flexible tubular second air line having an open distal free end and an open proximal end extended through the neck piece and secured to the upper extent of the bladder for supplying air thereto, wherein the flexible second air line is off set with respect to the central bore of the neck piece;

an air-fillable pilot balloon for providing an indication of a fill state of the bladder, the balloon having a sealable inlet for receiving air and an outlet coupled to the distal end of the second air line;

an electric pump for providing air for filling the pilot balloon and the bladder, the air pump having a hollow and box-shaped rigid metal housing with a plurality of feet extended downwards therefrom and positionable upon a recipient surface, the air pump further including a pneumatic diaphragm powered with a removable battery;

a microphone coupled to the neck piece and responsive to the user's voice; and an amplifier coupled to the microphone for amplifying the user's voice with an associated speaker.

* * * * *